United States Patent
Julin

(10) Patent No.: US 10,342,723 B2
(45) Date of Patent: Jul. 9, 2019

(54) EXOSKELETON CORD LOOP-TYPE ACTUATOR

(71) Applicant: Ekso Bionics, Inc., Richmond, CA (US)

(72) Inventor: Aaron Julin, Oakland, CA (US)

(73) Assignee: Ekso Bionics, Inc., Richmond, CA (US)

( * ) Notice: Subject to any disclaimer, the term of this patent is extended or adjusted under 35 U.S.C. 154(b) by 0 days.

(21) Appl. No.: 15/564,497

(22) PCT Filed: Apr. 6, 2016

(86) PCT No.: PCT/US2016/026117
§ 371 (c)(1),
(2) Date: Oct. 5, 2017

(87) PCT Pub. No.: WO2016/164395
PCT Pub. Date: Oct. 13, 2016

(65) Prior Publication Data
US 2018/0085277 A1    Mar. 29, 2018

Related U.S. Application Data

(60) Provisional application No. 62/193,901, filed on Jul. 17, 2015, provisional application No. 62/143,473, filed on Apr. 6, 2015.

(51) Int. Cl.
*A61H 1/02*    (2006.01)
*A61F 5/01*    (2006.01)
*F16H 19/06*   (2006.01)

(52) U.S. Cl.
CPC ......... *A61H 1/0262* (2013.01); *A61F 5/0102* (2013.01); *A61F 2005/0155* (2013.01);
(Continued)

(58) Field of Classification Search
CPC .......... A61H 1/0262; A61H 2201/1215; A61H 2201/165; A61H 2201/5069;
(Continued)

(56) References Cited

U.S. PATENT DOCUMENTS 3,172,127 A    3/1965 Tolotti
3,382,506 A    5/1968 Collins et al.
(Continued)

*Primary Examiner* — Quang D Thanh
(74) *Attorney, Agent, or Firm* — Diederiks & Whitelaw, PLC.

(57) ABSTRACT

An exoskeleton includes first and second support structures configured to be coupled to a wearer of the exoskeleton. A joint connects the first and second support structures, the joint enabling relative movement between the first and second structures. First and second cord loops connect the first and second support structures. At least one motor twists and thereby shortens the first and second cord loops, wherein shortening of the first cord loop causes relative movement of the first and second support structures about the joint in a first direction, and shortening of the second cord loop causes relative movement of the first and second support structures about the joint in a second, opposite direction. A brake mechanism prevents relative movement of the first and second support structures about the joint in at least one of the first and second directions if one of the first and second cord loops breaks.

12 Claims, 15 Drawing Sheets

(52) U.S. Cl.
CPC ............ *A61H 2201/0176* (2013.01); *A61H 2201/1215* (2013.01); *A61H 2201/1472* (2013.01); *A61H 2201/165* (2013.01); *A61H 2201/5069* (2013.01); *F16H 19/0654* (2013.01)

(58) Field of Classification Search
CPC .... A61H 2201/0176; A61H 2201/1472; A61H 1/02; A61H 1/0237; A61H 1/024; A61H 3/00; A61H 2001/0211; A61H 2003/007; A61H 2201/0157; A61H 2201/1073; A61H 2201/12; A61H 2201/1207; A61H 2201/1445; A61H 2201/164; A61H 2201/1642; A61H 2201/1671; A61H 2201/1673; A61H 2201/1676; A61H 2203/0406

See application file for complete search history.

(56) References Cited

U.S. PATENT DOCUMENTS

| | | |
|---|---|---|
| 3,826,251 A | 7/1974 | Ross |
| 4,038,706 A | 8/1977 | Ober et al. |
| 4,232,405 A | 11/1980 | Janovsky |
| 4,252,111 A | 2/1981 | Chao et al. |
| 4,359,207 A | 11/1982 | Maryonovich et al. |
| 4,456,003 A | 6/1984 | Allard et al. |
| 4,502,472 A | 3/1985 | Pansiera |
| 4,843,921 A * | 7/1989 | Kremer ............. A61F 2/54 74/89.2 |
| 7,543,690 B2 | 6/2009 | Eckenstein et al. |
| 7,722,555 B2 | 5/2010 | Doty et al. |
| 7,949,429 B2 | 5/2011 | Ohtera et al. |
| 8,123,709 B2 | 2/2012 | Deharde et al. |
| 8,237,390 B2 | 8/2012 | Godler |
| 8,256,310 B2 | 9/2012 | Godler |
| 8,500,823 B2 | 8/2013 | Herr et al. |
| 8,833,826 B2 | 9/2014 | Garcia et al. |
| 9,149,370 B2 | 10/2015 | Herr et al. |
| 9,266,233 B2 | 2/2016 | Kornbluh et al. |
| 9,566,173 B2 | 2/2017 | Ryu et al. |
| 9,693,926 B2 | 7/2017 | Goldfarb et al. |
| 2008/0066574 A1 | 3/2008 | Murata et al. |
| 2011/0199038 A1* | 8/2011 | Godler ............. B25J 9/126 318/568.12 |
| 2013/0046218 A1* | 2/2013 | Wiggin ............. A61F 5/0127 602/16 |
| 2013/0211297 A1* | 8/2013 | Method ............. A61H 1/024 601/34 |
| 2013/0289452 A1* | 10/2013 | Smith ............. B25J 9/0006 601/33 |
| 2014/0277739 A1* | 9/2014 | Kornbluh ............. B25J 9/0006 700/260 |
| 2015/0100006 A1 | 4/2015 | Lu |
| 2016/0107309 A1* | 4/2016 | Walsh ............. B25J 9/0006 248/550 |
| 2016/0128890 A1* | 5/2016 | LaChappelle ............. A61H 3/00 623/30 |

\* cited by examiner

EXOSKELETON CORD LOOP-TYPE ACTUATOR

CROSS-REFERENCE TO RELATED APPLICATIONS

This application represents a National Stage application of PCT/US2016/026117 filed Apr. 6, 2016 and titled "Exoskeleton Cord Loop-Type Actuator" which claims the benefit of U.S. Provisional Patent Application Ser. No. 62/143,473, which was filed on Apr. 6, 2015 and titled "Exoskeleton Joint Actuation Device with Integral Safety Mechanism", and U.S. Provisional Patent Application Ser. No. 62/193,901, which was filed on Jul. 17, 2015 and titled "Exoskeleton Joint Actuation Device with Integral Safety Mechanism and Reduced Wear". The entire content of these applications is incorporated by reference.

RESEARCH OR DEVELOPMENT

This invention was made with government support under Grant No. 1R43HD080236-01; FAIN: R43HD080236 awarded by the Eunice Kennedy Shriver National Institute of Child Health and Human Development. The government has certain rights in the invention.

FIELD OF THE INVENTION

The present invention relates to devices that augment a wearer's strength and/or aid in the prevention of injury during the performance of certain motions or tasks. More particularly, the present invention relates to devices suitable for therapeutic use with patients that have impaired neuromuscular/muscular function of the appendages or devices suitable for use by people engaging in heavy tool use or weight bearing tasks. Each of these devices includes a set of artificial limbs, with the artificial limbs being movable by actuators under the direction of a control system. The devices potentiate the function of a wearer's appendages for activities including, but not limited to, enabling walking for a disabled person, granting greater strength and endurance in the wearer's arms, or allowing for more weight to be carried by the wearer while walking.

BACKGROUND OF THE INVENTION

Wearable exoskeletons have been designed for medical, commercial, and military applications. Medical exoskeleton devices restore and rehabilitate proper muscle function for patients with disorders affecting muscle control. Medical exoskeleton devices have systems of motorized braces that can apply forces to a wearer's appendages. In a rehabilitation setting, medical exoskeletons are typically controlled by a physical therapist who uses one of a plurality of possible input means to command an exoskeleton control system. In turn, the exoskeleton control system actuates the position of the motorized braces, resulting in the application of force to, and typically movement of, the body of the wearer. Medical exoskeletons can also be used outside of a therapeutic setting to grant improved mobility to a disabled individual. Commercial and military exoskeletons are used to alleviate loads supported by workers or soldiers during their labor or other activities, thereby preventing injuries and increasing the stamina and strength of these workers or soldiers. Tool-holding exoskeletons are outfitted with tool-holding arms that support the weight of a tool, reducing user fatigue by providing tool-holding assistance. Each tool-holding arm transfers the vertical force required to hold the tool through the legs of the exoskeleton rather than through the wearer's arms and body. Similarly, weight-bearing exoskeletons transfer the weight of an exoskeleton load through the legs of the exoskeleton rather than through the wearer's legs. In some cases, weight-bearing exoskeletons are designed to carry a specific load, such as a heavy backpack. In other cases, military weight-bearing exoskeletons support the weight of armor. Commercial and military exoskeletons can have actuated joints that augment the strength of a wearer, with these actuated joints being controlled by an exoskeleton control system, and the wearer using any of a plurality of possible input means to command the exoskeleton control system.

In powered exoskeletons, exoskeleton control systems prescribe and control trajectories in the joints of the exoskeleton, resulting in movement of the exoskeleton. These trajectories can be prescribed as position-based, force-based, or a combination of both methodologies, such as those seen in impedance controllers. Position-based control systems can be modified directly through modification of the prescribed positions. Similarly, force-based control systems can be modified directly through modification of the prescribed force profiles. Complicated exoskeleton movements, such as walking in an ambulatory medical exoskeleton, are commanded by an exoskeleton control system through the use of a series of exoskeleton trajectories, with increasingly complicated exoskeleton movements requiring an increasingly complicated series of exoskeleton trajectories. These series of trajectories can be cyclic, such as the exoskeleton taking a series of steps with each leg, or they can be discrete, such as an exoskeleton rising from a seated position into a standing position. In the case of an ambulatory exoskeleton, during a rehabilitation session and/or over the course of rehabilitation, it is highly beneficial for the physical therapist to have the ability to modify the prescribed positions and/or the prescribed force profiles depending on the particular physiology or rehabilitation stage of a patient. As exoskeleton wearers are each differently proportioned, variously adjusted or customized powered exoskeletons will fit each wearer somewhat differently, requiring that the exoskeleton control system take into account these differences in wearer proportion, exoskeleton configuration/customization, and exoskeleton-wearer fit, resulting in changes to prescribed exoskeleton trajectories.

While exoskeleton control systems assign trajectories to the joints of exoskeletons and control the positions of these joints, the actual forces applied to exoskeleton joints are exerted by actuators. These actuators can take many forms, as is known in the art, each with advantages and disadvantages in various applications. In current exoskeletons, the actuator exerting force on a joint typically includes an electric motor located proximate to that joint. Co-location of the actuator with the joint has advantages in terms of mechanical and design simplicity, but it has certain disadvantages. Foremost among these disadvantages is that adding a bulky electric motor to a joint increases the bulk of the joint, limiting maneuverability of the joint and exoskeleton in certain environments. In comparison, consider a human finger. The musculature exerting force on the joints of the finger is not located near the joints of the finger but rather in the forearm, with muscular contraction pulling on tendons that relay the force over distance to the joints. This has the advantage of minimizing the bulk of the fingers, allowing for both greater dexterity and closer placement of the fingers to each other. In addition, more muscle can be located in the arm than would fit on the fingers, allowing for greater strength. One mechanical actuation device, described in U.S. Pat. No. 4,843,921, uses a drive mechanism in which an electric motor twists a loop of cord, with this cord loop forming a helical structure and shortening as it is twisted, thereby causing the length of the cord loop to shorten and pulling the two ends of the cord loop closer together. In this way, the activation of the electric motor is used to apply a pulling force over distance through the cord loop. This allows for a design in which the motor driving movement of a joint is located at a position distal from the joint being moved.

It is conceivable that a similar motor-and-loop drive system could be used to power the larger joints of a human exoskeleton, such as the knee of a human exoskeleton. One major advantage of this design would be a compact exoskeleton knee, which would reduce knee bulk and weight, allowing for a more maneuverable exoskeleton in cramped environments, such as getting in and out of a vehicle. However, there are also a number of disadvantages to such a design. First, the mechanisms of most robotic/exoskeleton actuators allow the actuator to exert force in two joint movement directions. In the case of the knee, those movement directions are flexion and extension. Unfortunately, the motor-and-loop drive system is only able to cause a pulling motion, such that force is only applied to a joint in one direction. While some embodiments of this type of actuator could use springs or other similar devices to cause a joint to return to a position when the current to the motor is disengaged, this is not suitable for the forces required to move the large joints of a human exoskeleton and the body of a wearer. In addition, even high tensile strength cord, after being twisted and untwisted many times or having been subject to stress from a fall or misstep, may be at risk of breakage. Failure of the cord would result in uncontrolled joint movement and an unacceptable chance of injury to an exoskeleton wearer. In the case of medical exoskeletons, this injury concern is particularly significant, as wearers can be subject to conditions resulting in little or no control over the movement of the knee or other joints. Furthermore, regulatory bodies, such as the Food and Drug Administration, require that medical devices comply with safety guidelines. Unless the risks of such a design are addressed, it is unlikely to be approved for use by these agencies.

Based on the above, there exists a need in the art for an exoskeleton in which an actuator makes use of a motor to twist a loop of cord in order to cause movement of an exoskeleton joint at a distance from the motor, with the joint being subject to bidirectional movements, and with movement of the joint being impeded in the event of cord breakage, thereby preventing injury to a wearer of the exoskeleton or further damage to the exoskeleton. There also exists an unmet need for an exoskeleton in which a joint is subject to bidirectional movements through the action of a single motor. In addition, there exists an unmet need for a device that controls the position and separation of the strands of the cord loop twisted by the actuator, with this device acting in such a way that the strands of the cord loop are subject to reduced wear with each twist cycle, thereby prolonging the functional lifespan of the cord loop.

SUMMARY OF THE INVENTION

It is an object of the present invention to provide an exoskeleton where force is exerted upon a joint of the exoskeleton by a system of cord loops that upon being twisted by an electric motor are shortened, resulting in the movement of the joint. Two opposing sets of cord loops and motors allow for movement of the joint in opposing directions. It is a further object of the present invention to provide an exoskeleton where movement of the joint is halted in the case of cord breakage, thereby preventing injury to an exoskeleton wearer. It is also an object of the present invention to provide an exoskeleton where the joint is subject to bidirectional movements through the action of only a single motor. To accomplish this, the exoskeleton includes one or more spring elements that act to prevent slack in the cord loop that can otherwise result over a range of cord loop twist amounts due to non-linear cord loop shortening as a function of twist. It is an additional object of the present invention to provide an exoskeleton where a device is shaped to guide and limit the helical cord structure formed at a transition region of the cord loop between twisted and untwisted sections, with the use of this device resulting in decreased cord loop wear and increased cord loop functional lifespan.

Concepts were developed for an exoskeleton joint and actuator device where the actuator's main drive mechanism is a pulley-and-cam assembly attached to two opposing sets of cord loops that, when one cord loop is shortened relative to the other, move the joint in opposite directions. When twisted by the connected electric motors, the cord loops form helical structures that are shortened with increasing twist, resulting in increased tension between an attachment point of the cord loop to the electric motor and an attachment point of the cord loop to a joint cam. Each of the two motors is connected to one of the cord loops, and each cord loop is attached to an opposite end of the joint cam such that the action of one motor results in joint movement opposite that caused by the other motor.

Concepts were further developed for the inclusion of a normally-on brake mechanism in which the cord loops attached to each side of the cam joint are routed across, and restrain the position of, a spring-loaded pulley. The pulleys are articulated through a small range of motion, and a set of spring-driven pawls are coupled to the pulleys. In the event of a loss of tension in either of the cord loops, the pulley and pawls are driven forward by the springs, and the pawls engage a section of a gear that is connected to the joint cam, thereby stopping joint rotation.

Concepts were further developed for the inclusion of mechanisms to prevent cord loop tangle in which cord loop twist is isolated to a linear portion of the cord loop, allowing the portion of the cord loop that engages with the pulley and cam to remain untwisted, and thereby providing better guidance of the cord loop and reduced wear.

Concepts were developed for a variant of the brake mechanism in which the normally-on brake design is configured such that both pulleys are connected to a single brake assembly. This brake assembly is spring-loaded, and the cord loops of the actuator are routed through the pulleys and tensioned in such a way as to restrain the movement of the brake assembly and compress the spring. In the event that either of the cord loops is broken, the force of the spring is such that the single remaining cord loop provides insufficient tension to restrain the movement of the brake assembly, and the brake assembly is driven forward by the spring until a section of gear attached to the brake assembly makes contact with a section of gear that is connected to the opposing joint cam, thereby locking the joint in place and stopping joint rotation.

Concepts were further developed for the inclusion of structures in cord loop spindles and cord strand separators that guide and restrict the strands of the cord loops and the helical structures formed at transition zones between twisted and untwisted sections of the cord loops in order to provide reduced cord loop wear, particularly at the transition zones.

Concepts were developed for a variant of the exoskeleton joint and actuator device where only one electric motor is used to drive the system in bidirectional joint movements, with this motor interacting with each cord loop through the use of gears connected to each cord loop spindle. The gears are configured such that action of the electric motor simultaneously drives one cord loop spindle clockwise and the other spindle counterclockwise, with the cord loops and spindles configured such that one cord loop is shortened as the opposing cord loop is lengthened. The spindles in this device are tensioned by spring elements that act to prevent slack in a cord loop that otherwise results over a range of cord loop twist amounts due to non-linear cord loop shortening as a function of twist.

Based on these concepts, an exoskeleton was developed having an exoskeleton knee actuation device with a braking mechanism that automatically engages in the event of cord loop breakage, thereby halting knee movement. In this arrangement, upper and lower leg supports are connected through the knee joint of the exoskeleton, and the actuators that affect movement of the knee are located near a hip of the exoskeleton.

In particular, the present invention is directed to an exoskeleton including first and second support structures configured to be coupled to a wearer of the exoskeleton. A joint connects the first and second support structures, the joint being configured to enable relative movement between the first and second structures. First and second cord loops connect the first and second support structures. At least one motor is configured to twist and thereby shorten the first and second cord loops, wherein shortening of the first cord loop causes relative movement of the first and second support structures about the joint in a first direction, and shortening of the second cord loop causes relative movement of the first and second support structures about the joint in a second, opposite direction. A brake mechanism is configured to prevent relative movement of the first and second support structures about the joint in at least one of the first and second directions if one of the first and second cord loops breaks.

In one embodiment, the brake mechanism includes a gear coupled to the second support structure and a first pawl coupled to the first support structure. The brake mechanism is configured such that the first pawl contacts the gear if the first cord loop breaks. Contact between the first pawl and the gear prevents relative movement of the first and second support structures about the joint in at least one of the first and second directions. The brake mechanism further includes a first pulley configured to contact the first cord loop and a first spring configured to apply a force to the first pawl. The brake mechanism is configured such that contact between the first pulley and the first cord loop prevents contact between the first pawl and the gear. The first spring causes the first pawl to contact the gear if the first cord loop breaks.

In another embodiment, the brake mechanism further includes a second pawl, a second pulley configured to contact the second cord loop and a second spring configured to apply a force to the second pawl. The brake mechanism is configured such that the second pawl contacts the gear if the second cord loop breaks. Contact between the second pawl and the gear prevents relative movement of the first and second support structures about the joint in at least one of the first and second directions. The brake mechanism is also configured such that contact between the second pulley and the second cord loop prevents contact between the second pawl and the gear. The second spring causes the second pawl to contact the gear if the second cord loop breaks.

In some embodiments, the at least one motor includes a first motor configured to twist the first cord loop and a second motor configured to twist the second cord loop. In other embodiments, the at least one motor includes a single motor configured to simultaneously twist, in opposite rotational directions, both the first and second cord loops. When a single motor is used, the exoskeleton can further include an input shaft, a first spindle coupled to the first cord loop and a second spindle coupled to the second cord loop. The motor is configured to cause rotation of the input shaft, and the input shaft is configured to cause rotation of the first and second spindles. The first spindle twists the first cord loop, and the second spindle twists the second cord loop. Preferably, a first spring reduces slack in the first cord loop, and a second spring reduces slack in the second cord loop.

In one embodiment, the exoskeleton further includes a spindle coupled to one of the first and second cord loops, the spindle including a cord slot and a first cord guide, wherein the one of the first and second cord loops passes through the cord slot and contacts the first cord guide. Preferably, the first cord guide is wedge-shaped such that no gap exists between the first cord guide and a twisted helical cord structure of the one of the first and second cord loops when the one of the first and second cord loops is twisted by the at least one motor. The exoskeleton can also include a strand separator including a second cord guide. The one of the first and second cord loops passes through the strand separator and contacts the second cord guide. The strand separator is configured such that a twisted helical cord structure of the one of the first and second cord loops only exists between the spindle and the strand separator when the one of the first and second cord loops is twisted by the at least one motor. Preferably, the second cord guide is wedge-shaped such that no gap exists between the second cord guide and the twisted helical cord structure when the one of the first and second cord loops is twisted by the at least one motor.

Additional objects, features and advantages of the invention will become more readily apparent from the following detailed description of the invention when taken in conjunction with the drawings wherein like reference numerals refer to corresponding parts in the several views.

DETAILED DESCRIPTION OF THE PREFERRED EMBODIMENTS

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

Figure 1:
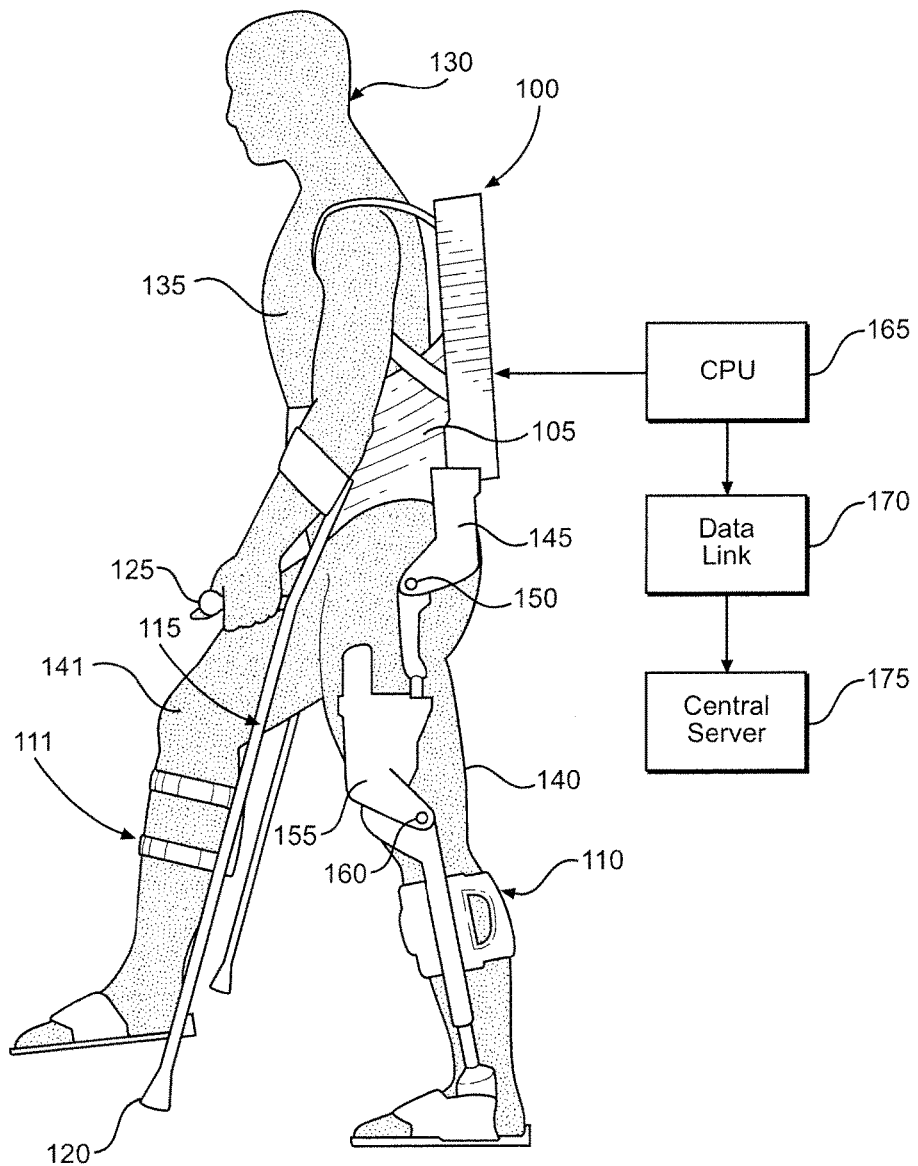
FIG. 1 is a side view of a handicapped individual coupled to an ambulatory exoskeleton, with actuators that control a joint being shown in close proximity to the joint.

With initial reference to FIG. 1, there is shown an exoskeleton 100 having a torso support 105 and lower leg supports 110 and 111. Exoskeleton 100 is used in combination with a pair of crutches, a left crutch 115 of which includes a lower, ground-engaging tip 120 and a handle 125. In connection with this embodiment, through the use of exoskeleton 100, a patient (or, more generally, a user or wearer) 130 is able to walk. In a manner known in the art, torso support 105 is configured to be coupled to a torso 135 of patient 130, while leg supports 110 and 111 are configured to be coupled to lower limbs 140 and 141 of patient 130. Additionally, actuators are interposed between portions of leg supports 110 and 111 as well as between leg supports 110 and 111 and torso support 105, with these actuators being configured to shift leg supports 110 and 111 relative to torso support 105 to enable movement of lower limbs 140 and 141 of patient 130. In some embodiments, torso support 105 can be quite small and comprise a pelvic link (not shown), which wraps around the pelvis of patient 130. In the example shown in FIG. 1, the actuators are specifically shown as a hip actuator 145, which is used to move a hip joint 150 in flexion and extension, and as a knee actuator 155, which is used to move a knee joint 160 in flexion and extension. Actuators 145 and 155 are controlled by a controller (or control system or CPU) 165 in a plurality of ways known to one skilled in the art of exoskeleton control. Although not shown in FIG. 1, various sensors are in communication with controller 165 so that controller 165 can monitor the orientation of exoskeleton 100. Such sensors can include, without restriction, encoders, potentiometers, accelerometer and gyroscopes, for example. In addition, controller 165 is in either continuous or intermittent communication with, and transfers selected exoskeleton state data to, a data link 170. Data link 170 is a wireless transmission device that is configured to transfer data received from controller 165 to a central server 175. As the additional structural particulars of exoskeletons can take various forms, are known in the art and are not part of the present invention, they will not be detailed further herein. Instead, exoskeleton 100 is intended to serve as an example of a prior art exoskeleton having actuators placed close to the joints being actuated. Specifically, as discussed above, hip actuator 145 is co-located with hip joint 150, and knee actuator 155 is co-located with knee joint 160.

Figure 2:
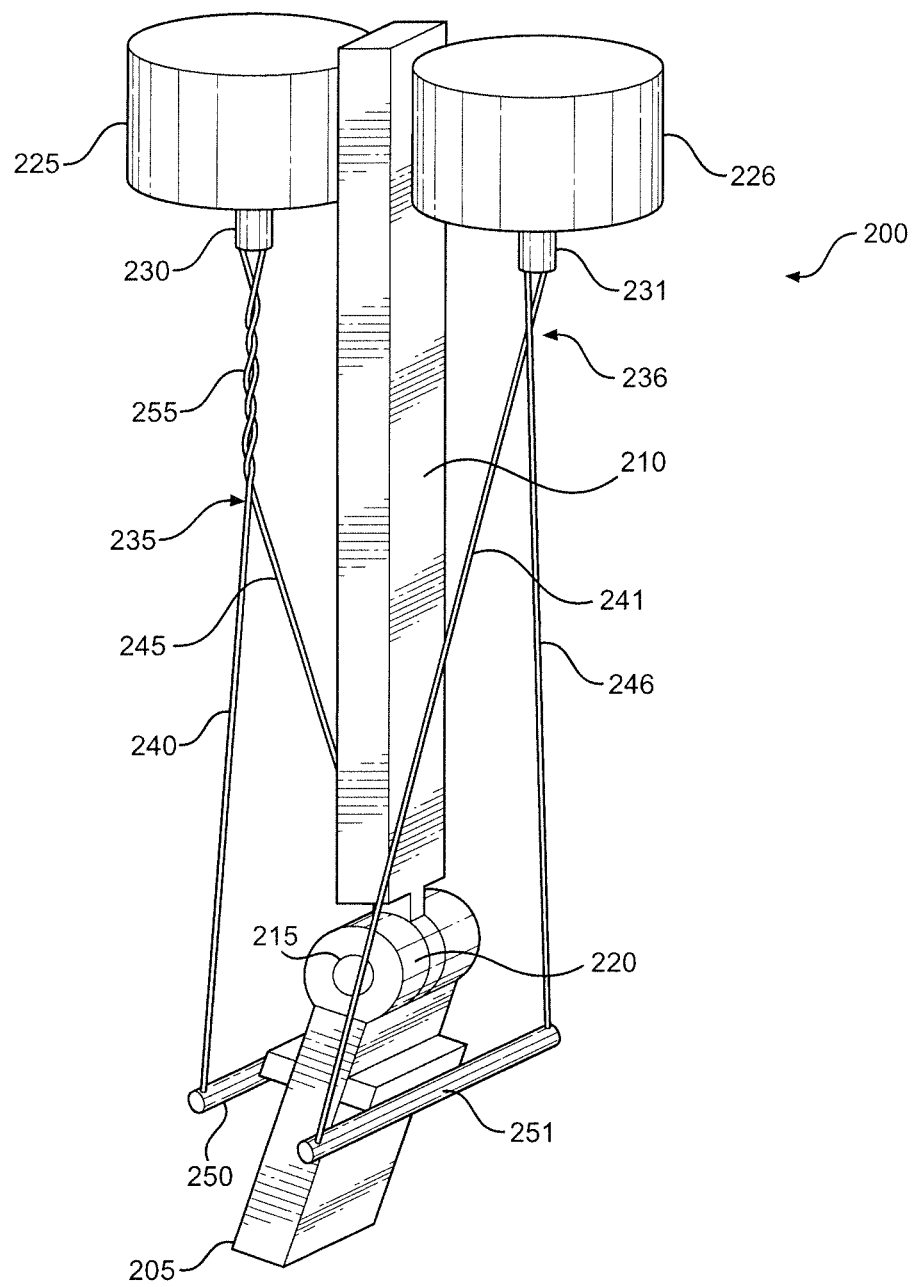
FIG. 2 is a perspective view of a simplified agonist-antagonist actuator device in accordance with the present invention in which the position of a joint is changed by the relative shortening of one of two cord loops as the cord loops are twisted by corresponding electric motors, with the action of each motor resulting in joint movement opposite that caused by the other motor.

Turning to FIG. 2, a simplified agonist-antagonist actuator 200 is shown in which a lower structure 205 is rotatably connected to an upper structure 210 by a joint bearing 215 at a joint 220. The position of lower structure 205 relative to upper structure 210 is controlled by the relative forces exerted by a left electric motor 225 and a right electric motor 226, which are coupled to upper structure 210. Left electric motor 225 controls the rotation of a left spindle 230. A left cord loop 235 passes through left spindle 230, left cord loop 235 including a first cord strand 240 and a second cord strand 245. First cord strand 240 and second cord strand 245 are coupled to a left cord acceptor 250, which is coupled to lower structure 205. Right electric motor 226 controls the rotation of a right spindle 231. A right cord loop 236 passes through right spindle 231, right cord loop 236 including a first cord strand 241 and a second cord strand 246. First cord strand 241 and second cord strand 246 are coupled to a right cord acceptor 251, which is coupled to lower structure 205. In FIG. 2, joint 220 is shown rotated such that lower structure 205 is positioned to the left of center, relative to upper structure 210, which is a result of left electric motor 225 being engaged and causing left spindle 230 to twist left cord loop 235. This results in the formation of a twisted helical cord structure 255, shortens the length of left cord loop 235 and increases the tension along left cord loop 235, such that left cord loop 235 exerts a pulling force on left cord acceptor 250. The force exerted on left cord acceptor 250, and therefore also on lower structure 205, results in a torque about joint 220. Conversely, if left electric motor 225 is disengaged and right electric motor 226 is engaged, right spindle 231 twists right cord loop 236, which results in a shortening of right cord loop 236 and torque about joint 220 such that lower structure 205 rotates counterclockwise relative to upper structure 210. This counterclockwise movement causes left spindle 230 to rotate and helical cord structure 255 to untwist such that the length of left cord loop 236 increases.

If actuator 200 were incorporated into an exoskeleton, both of cord loops 235 and 236 would be held under relatively high tension, and, as a result, any shortening of one loop should be compensated for by lengthening of the opposing loop. As such, an exoskeleton control system that accurately controls the current to each of electric motors 225 and 226 can accurately control the position of joint 220. This allows motors 225 and 226 to be placed at some distance from the joint being actuated, i.e., joint 220. In the simplified example of FIG. 2, both of motors 225 and 226 are shown on upper structure 210. However, many embodiments are possible, such as having both of motors 225 and 226 on the left side of joint 220, with one of motor 225 and 226 on upper structure 210 and one on lower structure 205. In some embodiments, multiple motors and loops are arrayed in parallel in order to increase the force exerted on a joint. In some embodiments, one or more spring elements are incorporated into a joint in order to assist in a return to a specific position.

Figure 3A:
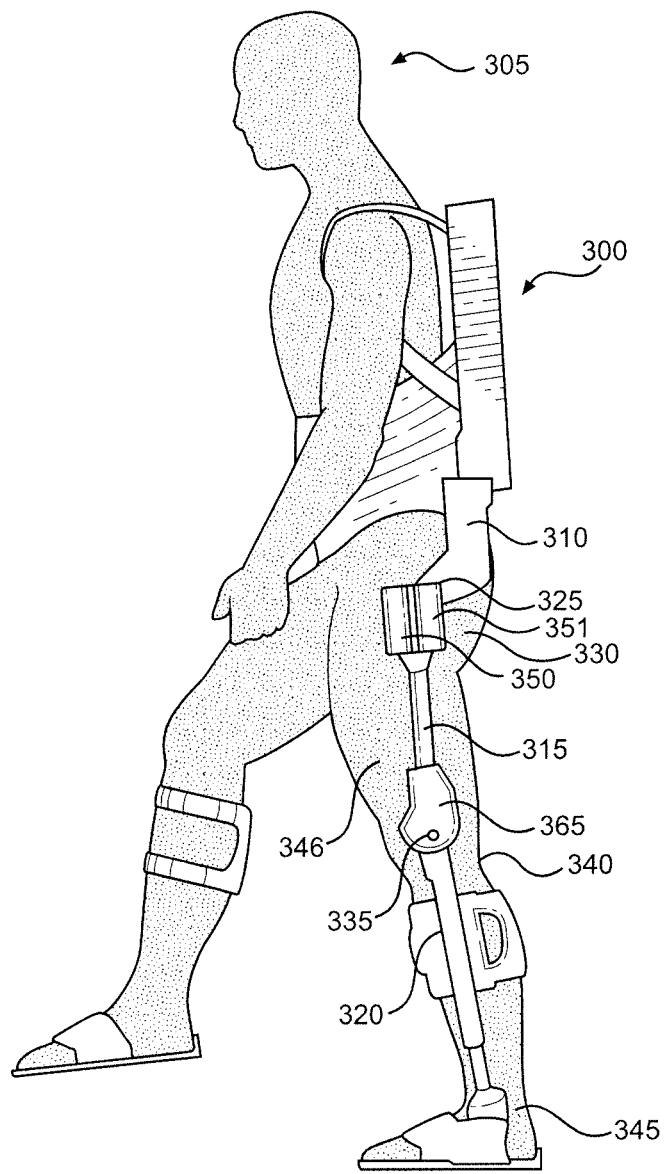
FIG. 3A is a side view of a handicapped individual coupled to an ambulatory exoskeleton in which a knee joint is actuated by an actuator device in accordance with a first embodiment of the present invention.
Figure 3B:
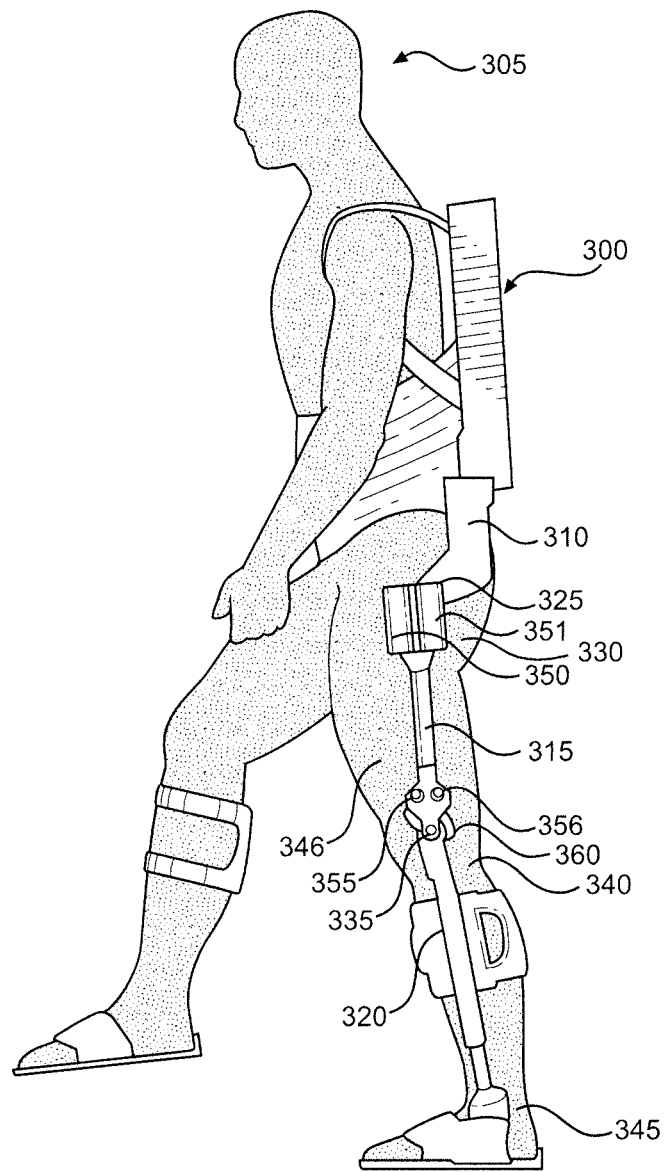
FIG. 3B is a side view of the handicapped individual and ambulatory exoskeleton of FIG. 3A, with a cover of a knee assembly removed.
Figure 4A:
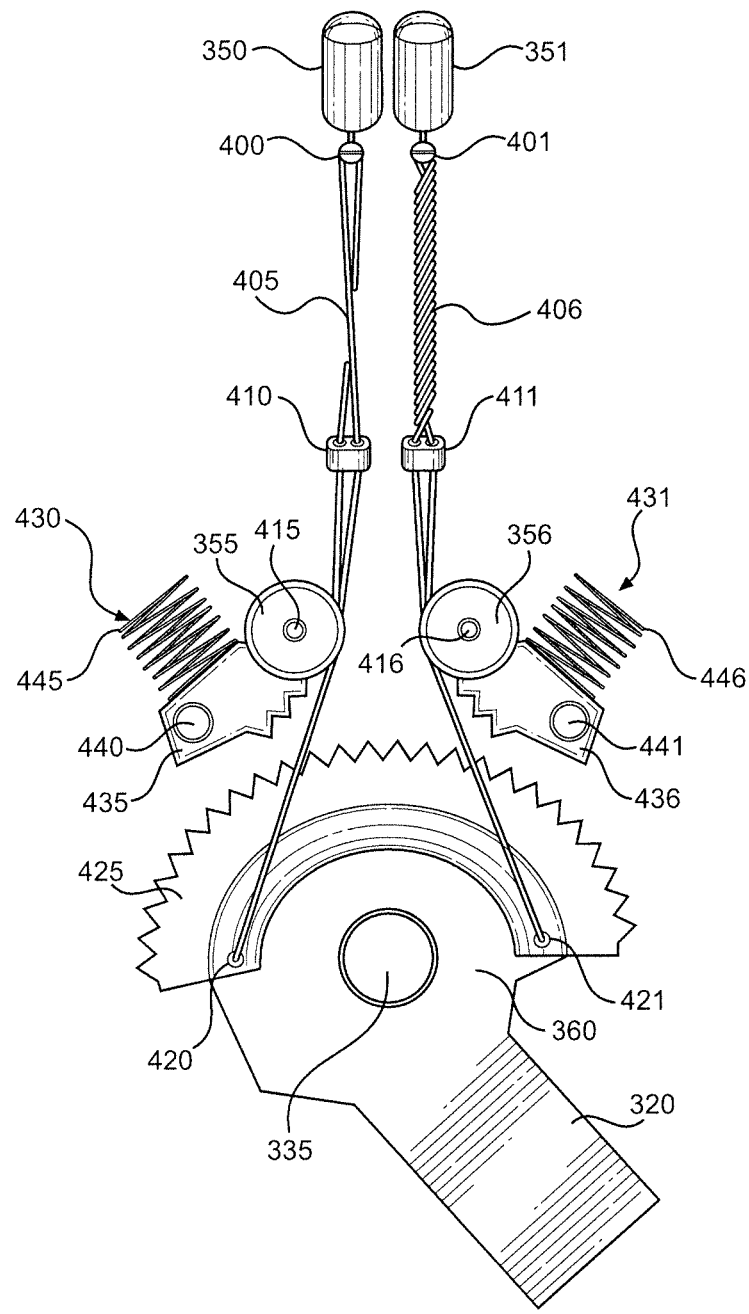
FIG. 4A is a simplified view of the actuator device of the first embodiment.
Figure 4B:
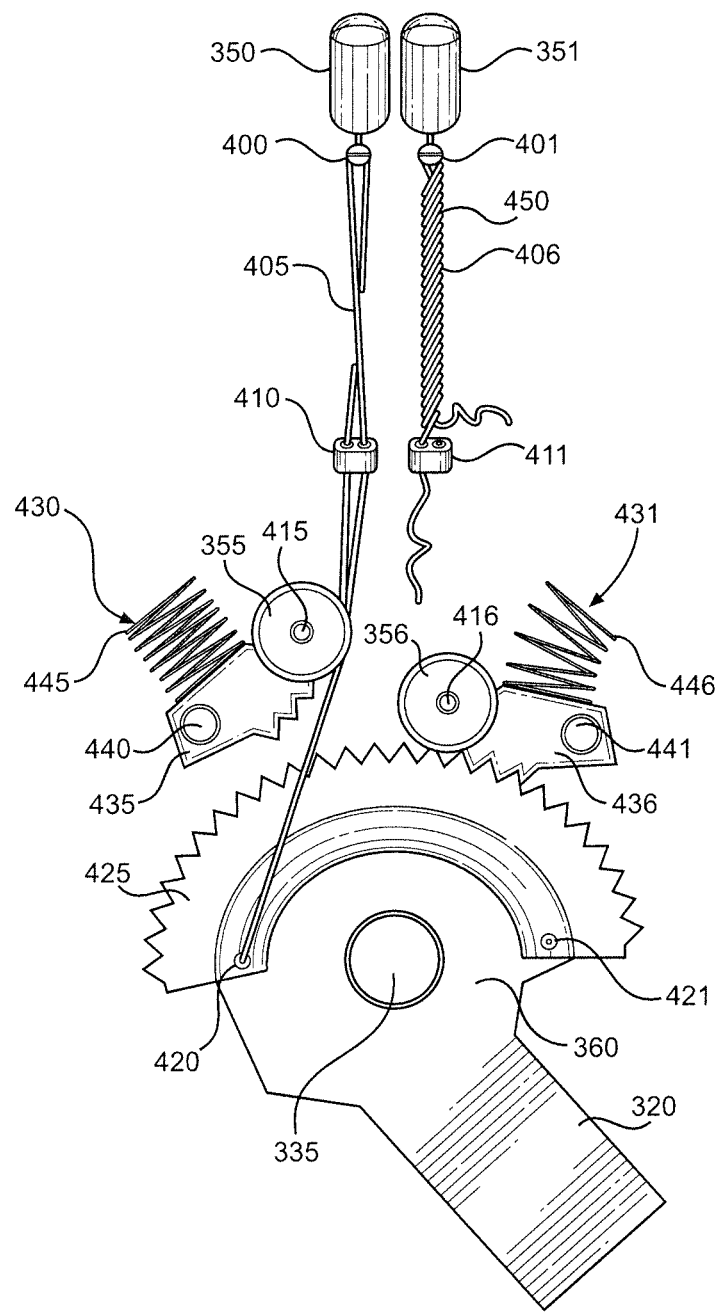
FIG. 4B is a simplified view of the actuator device of the first embodiment illustrating the position of braking components in response to breakage of one of the cord loops.

FIGS. 3A, 3B, 4A and 4B illustrate an actuator of a first embodiment of the present invention in a somewhat simplified fashion so as to facilitate a functional understanding of the actuator. FIGS. 3A and 3B show the actuator in the context of an exoskeleton being worn by a person, while FIGS. 4A and 4B show the inner workings of the major functional components of the actuator, which are not clearly visible in FIGS. 3A and 3B. Although the actuator is shown being used to power a knee joint of an exoskeleton, an actuator in accordance with the present invention can be used to provide actuation to a joint other than the knee of an exoskeleton or other similar robotic device. A much more detailed representation of an actuator in accordance with the first embodiment appears in FIG. 5, which is an exploded view of a particular actuator constructed in accordance with the invention.

Returning to FIGS. 3A and 3B, there is shown an exoskeleton 300 being worn by a user or wearer 305. Exoskeleton 300 includes a hip actuator 310, an upper leg support 315 and a lower leg support 320. Hip actuator 310 is rotatably connected to upper leg support 315 and configured to cause rotation of upper leg support 315 about a hip joint 325 that is co-located with a hip 330 of user 305. Upper leg support 315 is rotatably connected to lower leg support 320 at a knee joint 335 that is co-located with a knee 340 of user 305. Lower leg support 320 is configured to be selectively coupled to a lower leg 345 of user 305, while upper leg support 315 is configured to be selectively coupled to an upper leg 346 of user 305 (although this latter feature is not shown in the figures for the sake of clarity). Forward and rearward actuator motors 350 and 351 control the relative position of upper leg support 315 and lower leg support 320 through the use of cord loops, which are not visible in FIGS. 3A and 3B but are shown and discussed more fully in connection with FIGS. 4A and 4B. The cord loops pass through the center of upper leg support 315, with these cord loops being guided by and restraining the positions of a forward brake pulley 355 and rearward brake pulley 356, after which the cord loops connect to a knee cam 360 that is coupled to lower leg support 320. A cover 365 covers the inner working of knee joint 335 so as to prevent clothing or other materials from snagging on knee cam 360 or other brake components. In FIGS. 3A and 3B, motors 350 and 351 are shown co-located with hip 330 of user 305. In other embodiments, however, motors 350 and 351 can be located elsewhere along upper leg support 315 to decrease bulk or otherwise optimize space utilization. Alternatively, one or both of motors 350 and 351 can be located on lower leg support 320.

With particular reference to FIG. 4A, forward electric motor 350 is shown connected to a forward spindle 400. A forward cord loop 405 passes through forward spindle 400 and a forward strand separator 410. Also, forward cord loop 405 is in contact with forward brake pulley 355, which rotates about a forward pulley pin 415. Forward cord loop 405 is coupled to knee cam 360 of lower leg support 320 at a forward cord loop attachment point 420. Similarly, rearward electric motor 351 is connected to a rearward spindle 401. A rearward cord loop 406 passes through rearward spindle 401 and a rearward strand separator 411. Also, rearward cord loop 406 is in contact with a rearward brake pulley 356, which rotates about a rearward pulley pin 416. Rearward cord loop 406 is coupled to knee cam 360 at a rearward cord loop attachment point 421. Forward electric motor 350 and rearward electric motor 351 are coupled to upper leg support 315 (as shown in FIGS. 3A and 3B) such that a fixed distance is maintained between motors 350 and 351 and knee joint 335. A rack or gear 425 (e.g., a spur gear) is coupled to knee cam 360, with gear 425 and knee cam 360 rotating together about knee joint 335. A forward brake assembly 430 includes forward brake pulley 355, a forward pawl 435, a forward pivot pin 440 and a forward spring 445. Forward brake pulley 355 is rotatably coupled to forward pawl 435 by forward pulley pin 415. A rearward brake assembly 431 includes rearward brake pulley 356, a rearward pawl 436, a rearward pivot pin 441 and a rearward spring 446. Rearward brake pulley 356 is rotatably coupled to rearward pawl 436 by rearward pulley pin 416. Forward brake assembly 430 and rearward brake assembly 431 are rotatably coupled to upper leg support 315 (shown in FIGS. 3A and 3B) at forward pivot pin 440 and rearward pivot pin 441 respectively. Forward spring 445 and rearward spring 446 are held under compression against upper leg support 315 by forward pawl 435 and rearward pawl 436. The force required to compress springs 445 and 446 is exerted by tensioned cord loops 405 and 406 acting against brake pulleys 355 and 356.

In FIG. 4A, knee joint 335 is shown in flexion, which is the result of the action of rearward electric motor 351. Specifically, rearward electric motor 351 causes rotation of rearward spindle 401, which causes twisting of rearward cord loop 406 into a twisted helical cord structure 450 and shortening of the length of rearward cord loop 406. As a result, force is exerted on knee cam 360 such that lower leg support 320 rotates about knee joint 335 in the counter-clockwise direction. Helical cord structure 450 only extends to rearward strand separator 411, which is held in place such that rearward strand separator 411 is prevented from rotating. The section of rearward cord loop 406 below rearward strand separator 411 is untwisted, allowing rearward cord loop 406 to more easily, and with less wear or chance of catching, be routed over rearward brake pulley 356 to rearward cord loop attachment point 421. In the embodiment of FIGS. 3A, 3B, 4A and 4B, activation of forward electric motor 350 results in shortening of forward cord loop 405. As a result, force is exerted upon knee cam 360, which causes lower leg support 320 to move in extension. Therefore, forward electric motor 350, forward cord loop 405 and knee cam 360 can also be described as an extension actuator. Similarly, activation of rearward electric motor 351 results in shortening of rearward cord loop 406. As a result, force is exerted upon knee cam 360, which causes lower leg support 320 to move in flexion. Therefore, rearward electric motor 351, rearward cord loop 406 and knee cam 360 can also be described as a flexion actuator.

In FIG. 4B, breakage of rearward cord loop 406 is illustrated. Once this occurs, rearward brake pulley 356 is no longer restrained by rearward cord loop 406, and rearward spring 446 causes rearward pawl 436 to rotate about rearward pivot pin 441 until rearward pawl 436 contacts gear 425. At this point, the teeth of rearward pawl 436 mate with the teeth of gear 425. Since rearward pawl 436 is coupled to upper leg support 315 and gear 425 is coupled to lower leg support 320, the mating of these teeth prevents lower leg support 320 and upper leg support 315 from rotating relative to one another at knee joint 335. In the context of FIGS. 3A and 3B, the locking of knee joint 335 fixes the relative positions of lower leg 345 and upper leg 346 of user 305.

As an example of the first embodiment, consider an exoskeleton being worn by a recently disabled patient in a rehabilitation setting. The patient is engaged in exoskeleton therapy with the assistance of a physical therapist, and the exoskeleton is equipped with at least one joint that is powered by a cord loop-type actuator. If a cord loop of the actuator were to break and the exoskeleton was not equipped with the braking mechanism of the first embodiment, then the exoskeleton joint subject to the failure would be unrestrained and able to move freely. The patient wearing the exoskeleton, who might have little or no strength in the joint co-located with the exoskeleton joint where the failure occurred, would be at substantial risk of injury or falling. By making use of the braking mechanism of the first embodiment, if a cord breakage were to occur, then the braking mechanism would automatically engage, locking the joint in place and greatly reducing the risk of injury to the patient. In the case of exoskeletons being used as medical devices, such as those being used in gait training or other exoskeleton therapy, the assurance of safety is a prerequisite to regulatory approval by the Food and Drug Administration and other regulatory bodies. The normally-on nature of the braking mechanism also has the benefit of conserving battery power when a fixed position state is desired at the knee or other joint as, unlike with a typical exoskeleton joint actuator, there is no need to send current to motors to react to external force inputs. This lack of a requirement for current serves a further safety feature since the braking mechanism can still function in the event of an exoskeleton power failure. Also, since these therapeutic exoskeletons can be used outside of a clinic as mobility devices (e.g., as a wheelchair replacement), the reduced bulk of the joint is beneficial for preventing the joint from catching on clothing or obstacles and for facilitating the entry and exit of automobiles, for example.

Figure 5:
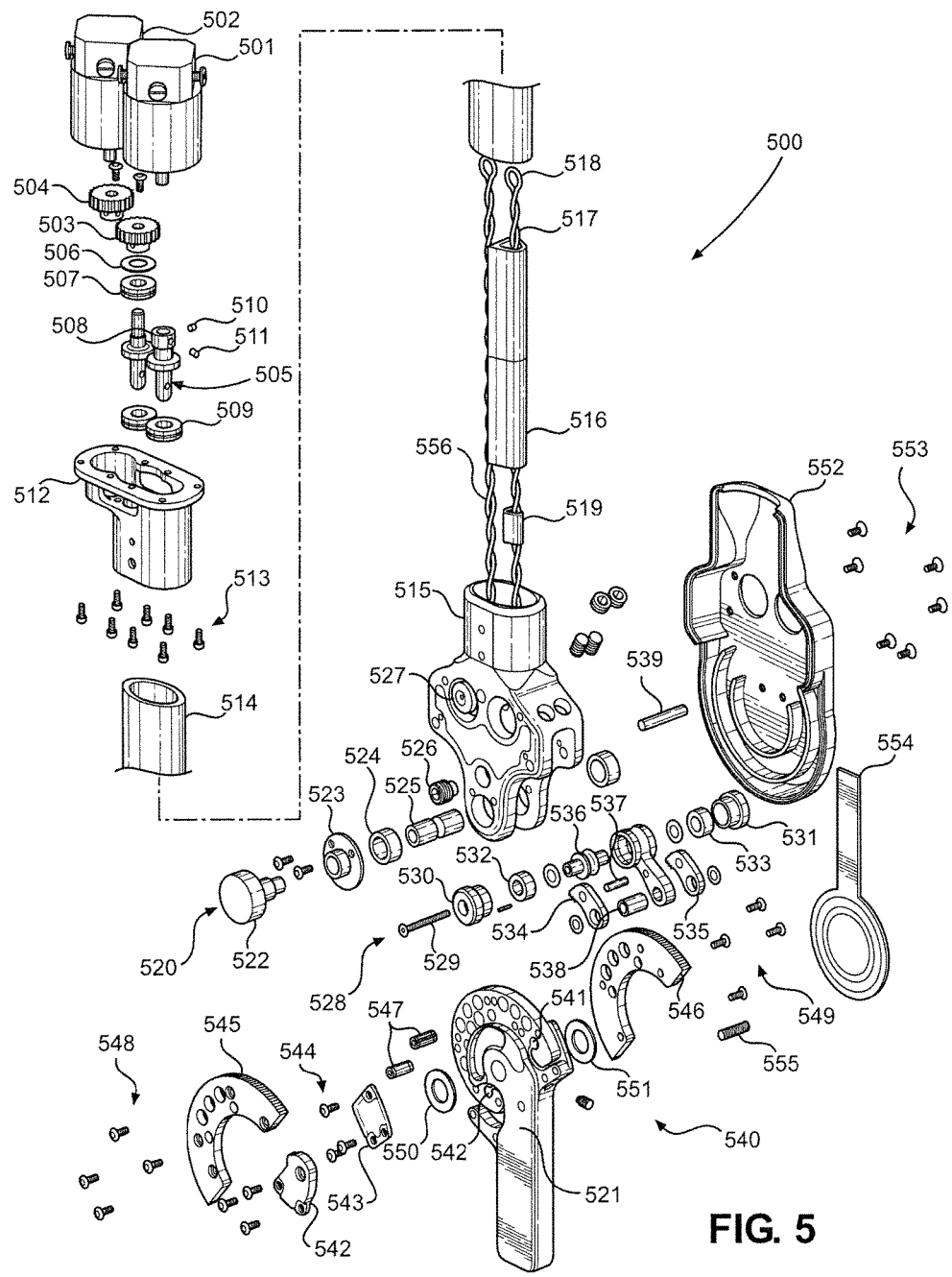
FIG. 5 is a detailed, exploded view of an actuator device constructed in accordance with the first embodiment of the present invention.

As noted above the exoskeleton illustrated in FIGS. 3A, 3B, 4A and 4B is a somewhat simplified representation intended to facilitate an understanding of the present invention. A more detailed representation is provided in FIG. 5, which shows a device constructed in accordance with the first embodiment. Unlike exoskeleton 100 of FIGS. 3 and 4, the device shown in FIG. 5 includes two gears, one on each side of the joint cam, and four pawls, each in contact with one of four springs, with two pawls on each side of the brake assembly. As a result, in the event of cord loop breakage, a brake assembly will lock a pawl into each gear. In addition, the gears on each side of the joint cam function as a guide for the cord loop to the cam attachment points. It should be noted that, in some cases, only the paired parts are shown in more detail for either the extension or flexion component, e.g., the extension brake assembly is shown in exploded view, while the flexion brake assembly is shown as an assembled unit. Also shown in FIG. 5 are sensors that relay information on joint state to an exoskeleton control system. In the arrangement of FIG. 5, the pawls are unidirectional, with the pawl on a joint extension pulley counteracting joint flexion, and vice-versa. In other embodiments, the brake mechanism is designed so that the pawls stop motion in either direction or so that a single pawl is coupled to both of the pulleys and acts when tension is lost in either (or both) cord loops. The arrangement shown in FIG. 5 was selected, at least in part, based on avoidance of self-locking situations and ease of control algorithm design.

More specifically, a cord loop-type actuator 500 of FIG. 5 includes an extension electric motor 501 and a flexion electric motor 502 that interface with a first gear 503 and a second gear 504, respectively. Gear 503 is a component of an extension spindle 505, which includes a shim washer 506, a roller bearing 507, a direct-drive spindle 508 and a thrust bearing 509. Set screws 510 and 511 fasten together the components of extension spindle 505. Electric motors 501 and 502 are coupled to a motor mount 512 by fasteners (collectively labeled 513), with motor mount 512 being coupled to extruded tubing 514, which is coupled in turn to a joint body 515. Within extruded tubing 514 is an extension separator guide 516, which contains a high-strength extension cord loop 517 that connects to extension spindle 505 at an extension cord loop connector 518. Extension cord loop 517 passes through an extension strand separator 519, which is able to slide along the length of extension separator guide 516, with extension separator guide 516 preventing the rotation of extension strand separator 519. A joint 520 (which is a knee joint in this example) connects joint body 515 to a joint cam 521. Joint 520 includes a rheostat potentiometer 522, a potentiometer mount 523, a needle roller bearing 524 and a joint shaft 525. A dog point screw 526 restricts movement of joint cam 521 relative to joint body 515, setting the terminal allowable points for knee joint extension and flexion.

A flexion brake assembly 527 is shown assembled and positioned within joint body 515, while the components of an extension brake assembly 528 are shown in exploded view. Extension brake assembly 528 includes a brake fastener 529, a pulley caps 530 and 531, roller bearings 532 and 533, brake pawls 534 and 535, a pulley 536, a dowel pin 537, a bearing 538, and a dowel pin 539. Dowel pin 539 constitutes the pivot for extension brake assembly 528. A lower joint assembly 540 includes joint cam 521, which has an extension cord loop attachment point 541 and a flexion cord loop attachment point 542. Cord loop termination covers 542 and 543 are coupled to joint cam 521 by fasteners (collectively labeled 544). Gears 545 and 546 are coupled to joint cam 521 by spring pins (collectively labeled 547) and fasteners (collectively labeled 548 and 549). Washers 550 and 551 are in contact with both joint cam 521 and joint body 515.

Although actuator 500 includes two joint covers, only one is shown for clarity. In particular, a joint cover 552 is coupled to joint body 515 with fasteners (collectively labeled 553) and covers both joint body 515 and lower joint assembly 540. A ring potentiometer 554 is coupled to the inner face of joint cover 552, and a spring plunger 555 interfaces with ring potentiometer 554 to allow for joint angle sensing. It should be noted that actuator 500 contains redundant joint angle sensing systems, specifically, rheostat potentiometer 522 and ring potentiometer 554. Preferably, only ring potentiometer 554 is included in practice. The inclusion of rheostat potentiometer 522 can be considered beneficial since rheostat potentiometer 522 is functional without joint cover 552 being in place. It should also be noted that gears 545 and 546, in addition to functioning as part of the braking mechanism, act to guide extension cord loop 517 and a corresponding flexion cord loop 556 onto joint cam 521.

Figure 6:
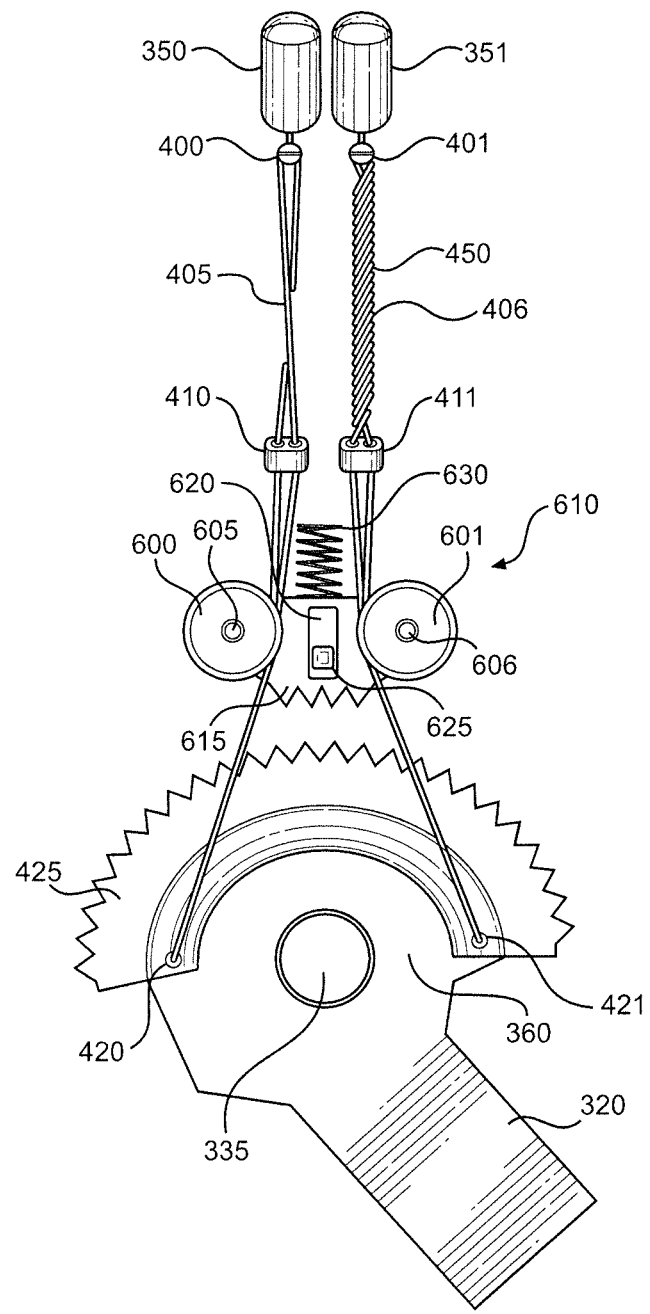
FIG. 6 is a simplified view of an actuator device in accordance with a second embodiment of the present invention.
Figure 7C:
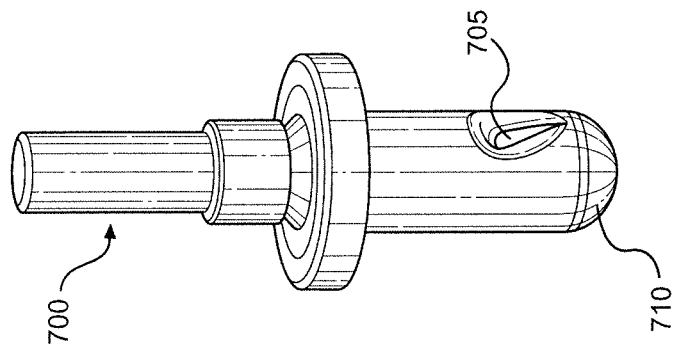
FIG. 7C is a perspective view of the spindle of FIG. 7A.
Figure 7B:
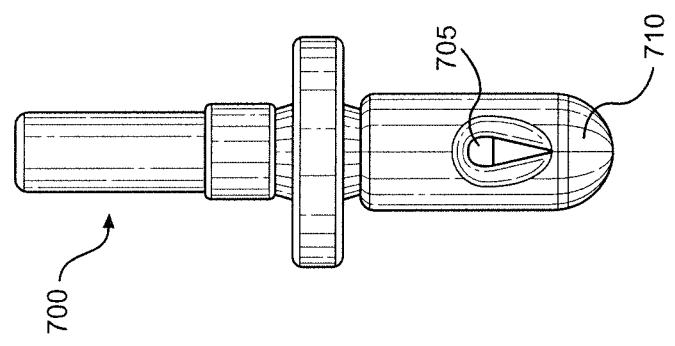
FIG. 7B is a side view of the spindle of FIG. 7A rotated 90 degrees in a vertical plane relative to FIG. 7A.
Figure 7A:
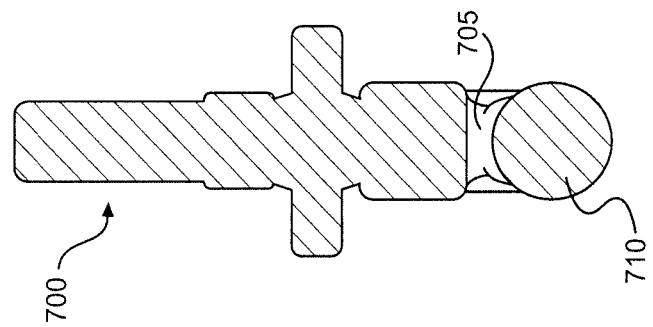
FIG. 7A is a cross section of a spindle, about which a cord loop of the present invention is twisted, in accordance with a first spindle embodiment.

With reference now to FIG. 6, a second embodiment of the present invention is shown. As in FIGS. 3A, 3B, 4A and 4B, forward electric motor 350 is connected to forward spindle 400, and forward cord loop 405 passes through forward spindle 400 and forward strand separator 410. Also, forward cord loop 405 is in contact with a forward brake pulley 600, which rotates about a forward pulley pin 605. Forward cord loop 405 is coupled to knee cam 360 of lower leg support 320 at a forward cord loop attachment point 420. Similarly, rearward electric motor 351 is connected to rearward spindle 401. Rearward cord loop 406 passes through rearward spindle 401 and rearward strand separator 411. Also, rearward cord loop 406 is in contact with a rearward brake pulley 601, which rotates about a rearward pulley pin 606. Rearward cord loop 406 is coupled to knee cam 360 at rearward cord attachment point 421. Forward electric motor 350 and rearward electric motor 351 are coupled to upper leg structure 315 (as shown in FIGS. 3A and 3B) such that a fixed distance is maintained between motors 350 and 351 and knee joint 335. A gear 425 is coupled to knee cam 360, with gear 425 and knee cam 360 rotating together about knee joint 335. A brake assembly 610 includes forward brake pulley 600, rearward brake pulley 601, a gear 615, a slot 620, a slot guide 625 and a spring 630. Slot guide 625 is located at a fixed position between knee joint 335 and motors 350 and 351. Also, slot guide 625 is in tight contact with the sides of slot 620 such that brake assembly 610 is unable to rotate relative to slot guide 625. However, brake assembly 610 is able to slide a short distance along slot guide 625 within the length of slot 620. Spring 630 abuts a portion of exoskeleton (e.g., upper leg support 315) and applies a force to brake assembly 610, with this force being resisted and the motion of brake assembly 610 along slot guide 625 being restrained by the tension applied to forward brake pulley 600 and rearward brake pulley 601 by forward cord loop 405 and rearward cord loop 406. In the event of breakage of either forward cord loop 405 or rearward cord loop 406, the tension applied by the remaining cord loop is insufficient to resist the force of spring 630 such that brake assembly 610 is driven forward along slot guide 625 until gear 615 makes contact with gear 425. This results in a locking of knee joint 335, with movement of knee joint 335 in either direction being prevented.

As an example of the second embodiment, consider an exoskeleton being worn by a recently disabled patient in a rehabilitation setting. The patient is engaged in exoskeleton therapy with the assistance of a physical therapist, and the exoskeleton is equipped with at least one joint that is powered by a cord loop-type actuator. If a cord loop of the actuator were to break and the exoskeleton was not equipped with the braking mechanism of the second embodiment, then the exoskeleton joint subject to the failure would be unrestrained and able to move freely. The patient wearing the exoskeleton, who might have little or no strength in the joint co-located with the exoskeleton joint where the failure occurred, would be at substantial risk of injury or falling. By making use of the braking mechanism of the second embodiment, if a cord breakage were to occur, then the braking mechanism would automatically engage, locking the joint in place and greatly reducing the risk of injury to the patient. In the case of exoskeletons being used as medical devices, such as those being used in gait training or other exoskeleton therapy, the assurance of safety is a prerequisite to regulatory approval by the Food and Drug Administration and other regulatory bodies.

Figure 8C:
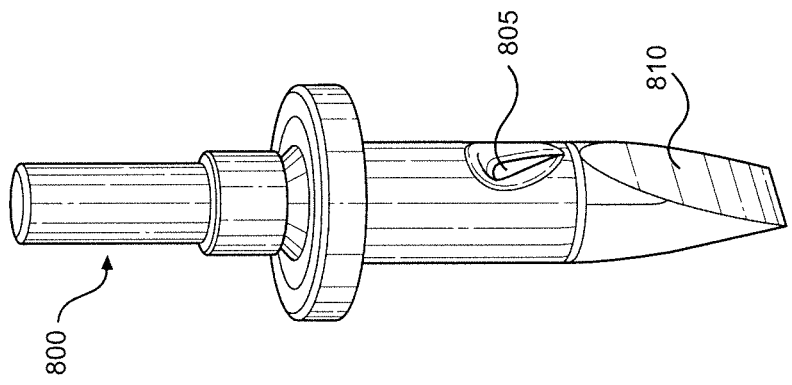
FIG. 8C is a perspective view of the spindle of FIG. 8A.
Figure 8B:
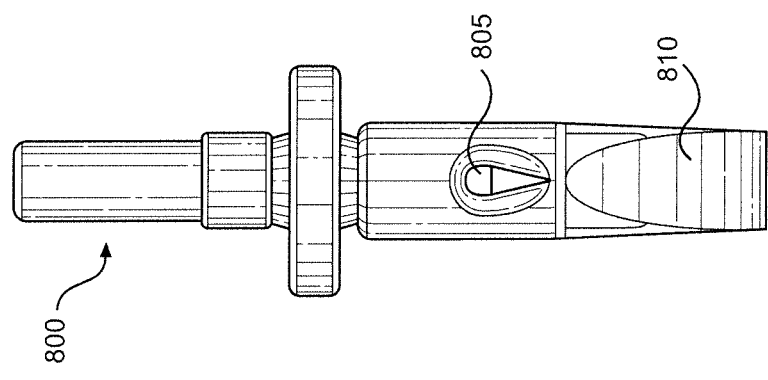
FIG. 8B is a side view of the spindle of FIG. 8A rotated 90 degrees in a vertical plane relative to FIG. 8A.
Figure 8A:
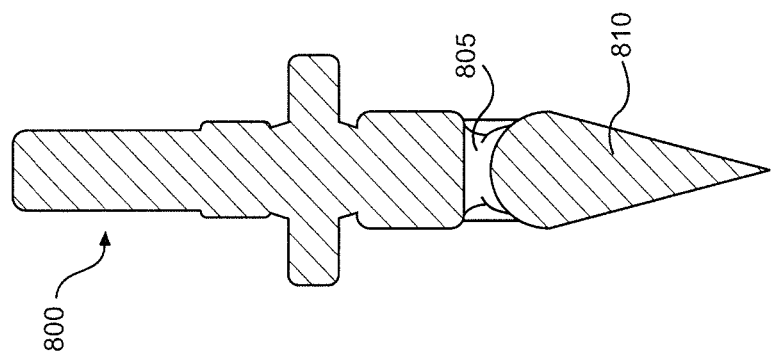
FIG. 8A is a cross section of a spindle, about which a cord loop of the present invention is twisted, in accordance with a second spindle embodiment.
Figure 9B:
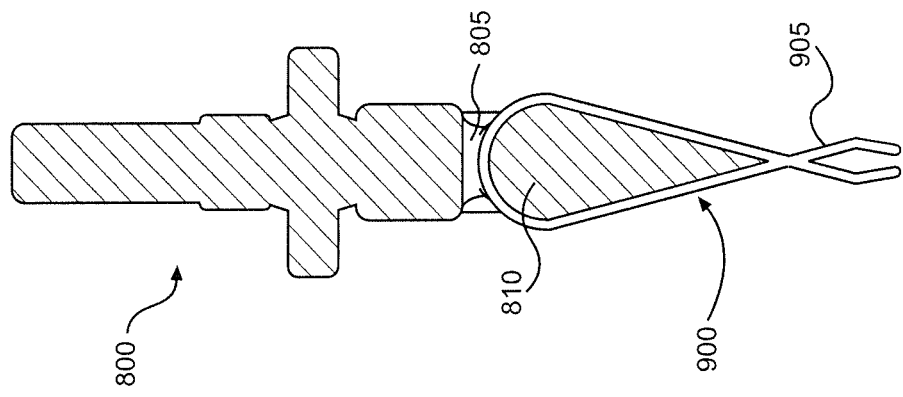
FIG. 9B is a cross section of the spindle of FIG. 8A, with a cord loop shown twisted about the spindle.
Figure 9A:
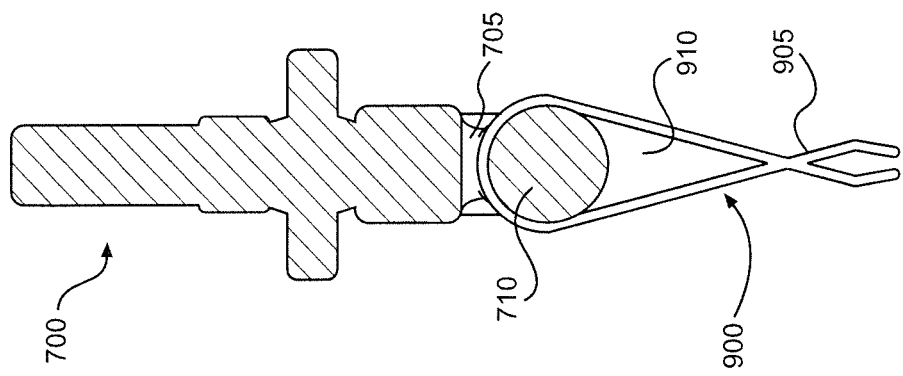
FIG. 9A is a cross section of the spindle of FIG. 7A, with a cord loop shown twisted about the spindle.

Turning to FIGS. 7A-C and 8A-C, there are shown first and second spindle embodiments for use in connection with the present invention. Specifically, in FIGS. 7A-C, a spindle 700 includes a cord slot 705 and a rounded cord guide 710. In FIGS. 8A-C, a spindle 800 includes a cord slot 805 and a wedge-shaped cord guide 810. FIGS. 9A and 9B respectively show spindles 700 and 800 with a cord loop 900 at high twist due to the action of an electric motor, which results in the formation of a twisted helical cord structure 905 (as discussed above). Spindle 700 has a gap 910 between its surface and helical cord structure 905 due to the round shape of cord guide 710. In contrast, spindle 800 has no gap between its surface and helical cord structure 905 due to the wedge shape of cord guide 810. The elimination of this gap is advantageous due to the additional control and support, thereby reducing wear. In some embodiments, cord guide 810 is a separate piece coupled to spindle 800. In one preferred embodiment, cord guide 810 is made of a soft material that allows for some degree of deformation.

Figure 10B:
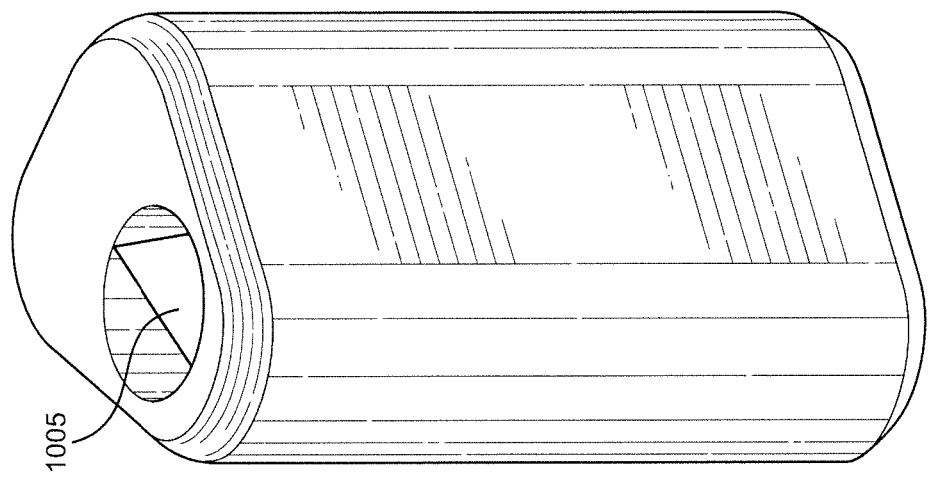
FIG. 10B is a perspective view of the cord loop strand separator of FIG. 10A.
Figure 10A:
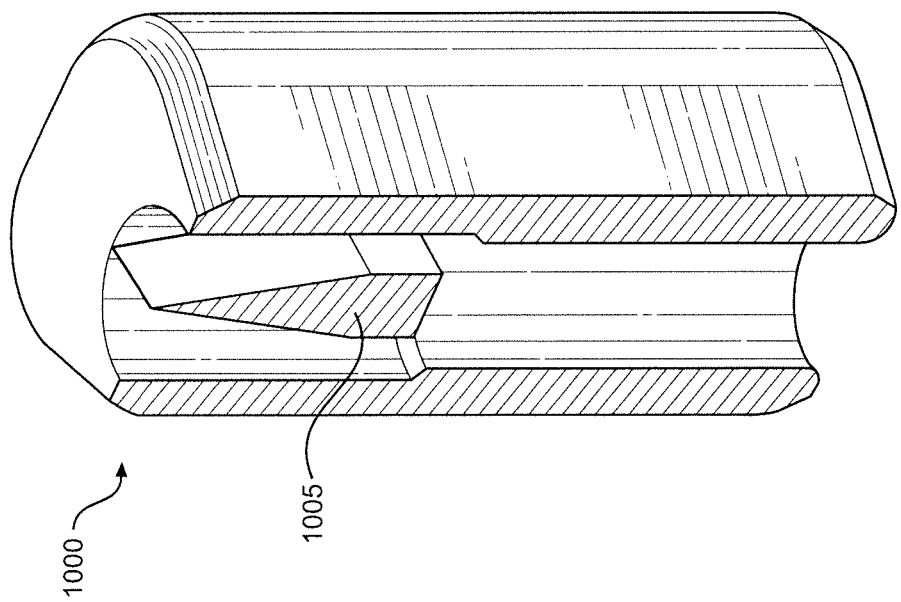
FIG. 10A is a cross section of a cord loop strand separator in accordance with the present invention.

FIGS. 10A and 10B show a cord loop strand separator 1000 for use in connection with the present invention. As discussed above, a cord loop passes through a strand separator, with a twisted helical cord structure of the cord loop being located between a spindle at one end and the strand separator at the other end. The strand separator is configured to separate the strands of the cord loop such that the helical cord structure does not continue past the strand separator, i.e., the portion of the cord loop after strand separator is untwisted. This allows the cord loop to more easily, and with less wear or chance of catching, be routed over a brake pulley to a cord loop attachment point. Returning to strand separator 1000 specifically, strand separator 1000 includes a wedge-shaped cord guide 1005, which functions in a manner similar to that of cord guide 810. In particular, as with cord guide 810, cord guide 1005 prevents the formation of a gap between the helical cord structure and the surface of strand separator 1000.

As an example of the utility of the spindles and cord loop strand separators of the present invention, consider an exoskeleton with a knee joint and actuator of the type shown in connection with the first embodiment of the present invention. Over many cycles of cord loop twist and untwist, the surface of the cord loop will begin to degrade, particularly at the transition regions between twisted and untwisted portions of the cord loop. Through the use of the spindles and strand separators of the present invention, wear on the cord loop in these transitional twisted-to-untwisted regions is substantially decreased. Testing of these structures has shown decreased cord loop wear relative to a device of the first embodiment that does not utilize them, with cord loop wear being readily observable as a function of fiber fray and breakage on the surface of the cord loop. Decreased cord loop wear reduces the maintenance needs of the exoskeleton and the chance of the exoskeleton being temporarily disabled while in use due to cord loop breakage. The cord loops of the present invention can be made from a variety of materials. However, preferred materials include HMPE (High Modulus Polyethylene), LCP (Liquid Crystal Polymer), ARAMID (Aromatic Polyamide), and PBO (Polybenzoxazole).

Figure 11A:
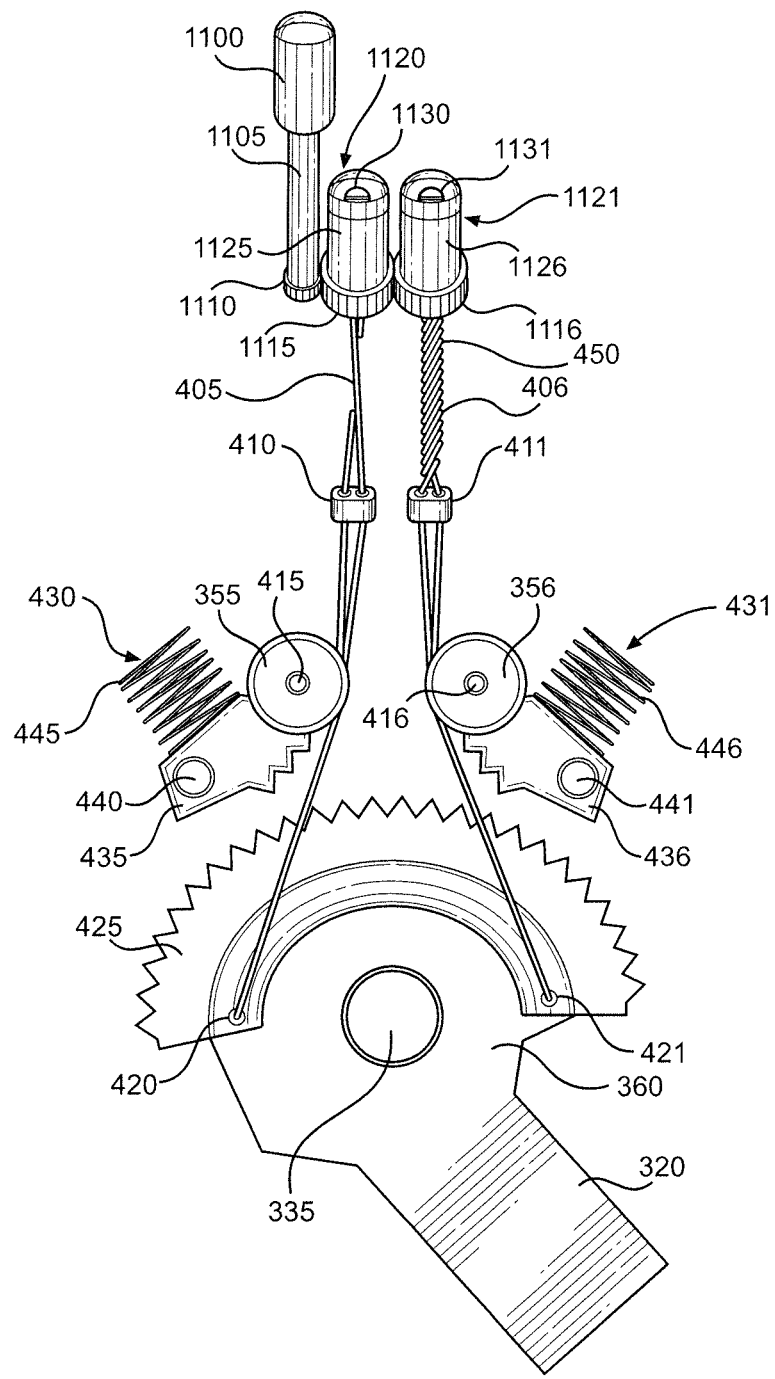
FIG. 11A is a simplified view of an actuator device in accordance with a third embodiment of the present invention.
Figure 11B:
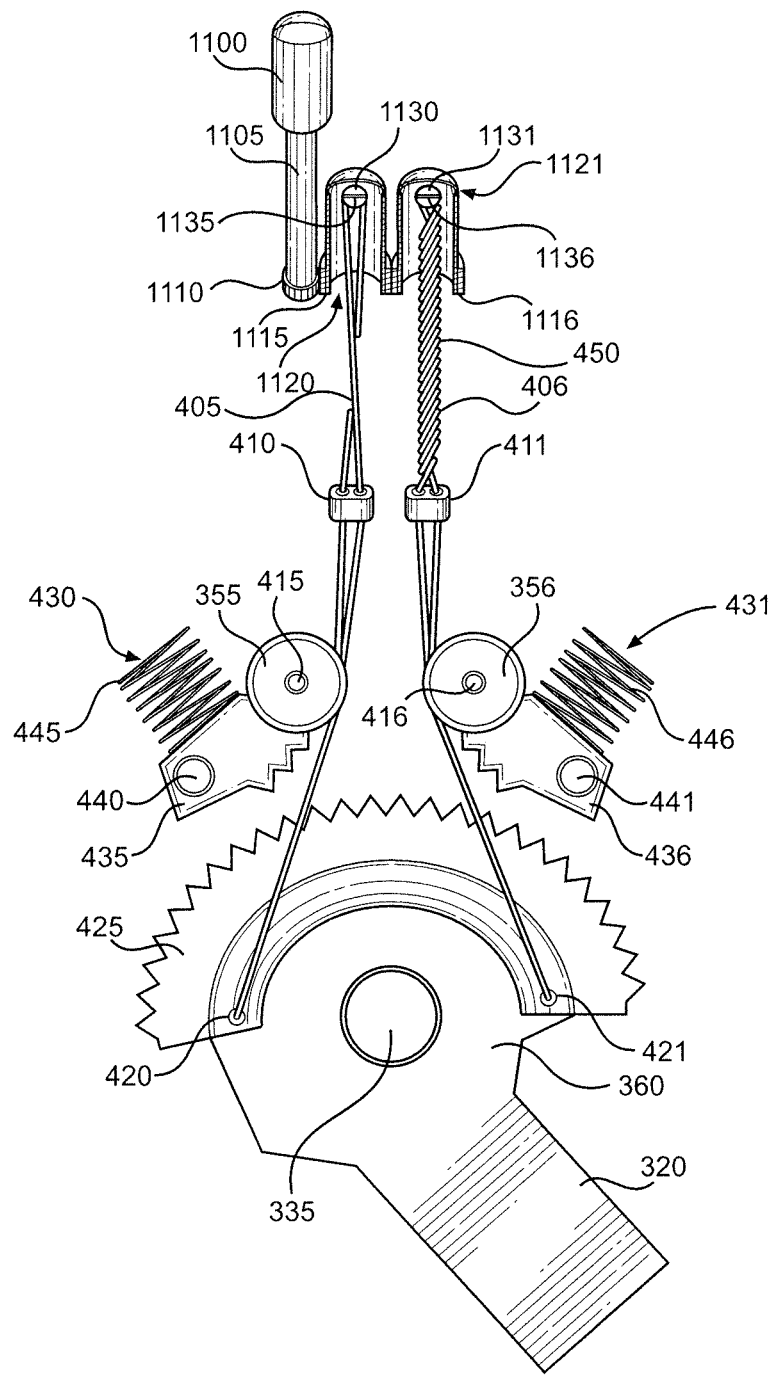
FIG. 11B is a simplified view of the actuator device of FIG. 11A showing internal spindle components.

With reference now to FIGS. 11A and 11B, there is shown an actuator in accordance with a third embodiment of the present invention. A bidirectional electric motor 1100 drives the rotation of an input shaft 1105. A drive gear 1110 on input shaft 1105 contacts a forward gear 1115 of a forward spindle 1120. A rearward spindle 1121 includes a rearward gear 1116 that is in contact with forward gear 1115. Forward spindle 1120 includes a forward elastomer spring 1125 and a forward spring termination pin 1130. Forward spring termination pin 1130 passes through forward cord loop 405 and limits the position of forward cord loop 405 and a forward cord loop apex 1135. Rearward spindle 1121 includes rearward elastomer spring 1126 and a rearward spring termination pin 1131. Rearward spring termination pin 1131 passes through rearward cord loop 406 and limits the position of rearward cord loop 406 and a rearward cord loop apex 1136. As a result of the connection between drive gear 1110, forward gear 1115 and rearward gear 1116, counterclockwise rotation of drive gear 1110 causes clockwise rotation of forward gear 1115, which in turn causes counterclockwise rotation of rearward gear 1116. Clockwise rotation of forward gear 1115 also causes clockwise rotation of forward spindle 1120 and forward spring termination pin 1130, which results in forward cord loop 405 twisting and shortening. The simultaneous counterclockwise rotation of rearward spindle 1121 and rearward spring termination pin 1131 results in rearward cord loop 406 untwisting and lengthening. Thus, the activation of motor 1100 in a counterclockwise direction simultaneously lengthens rearward cord loop 406 and shortens forward cord loop 405. Since motor 1100 and spindles 1120 and 1121 are connected to upper leg support 315 (shown in FIGS. 3A and 3B), which maintains a fixed distance between these structures and knee joint 335, the simultaneous lengthening of rearward cord loop 406 and shortening of forward cord loop 405 results in decreased tension on rearward cord loop attachment point 421 and increased tension on forward cord loop attachment point 420, which causes lower leg support 320 to rotate forward about knee joint 335, i.e., in a clockwise direction. Similarly, the activation of motor 1100 in a clockwise direction causes lower leg support 320 to rotate rearward about knee joint 335, i.e., in a counterclockwise direction. Forward and rearward elastomer springs 1125 and 1126 are beneficial in this design since the shortening and lengthening of cord loop 405 and 406 is not a linear function. This is not an issue in the first and second embodiments since the opposing motors can be used to take up any slack. However, when cord loops 405 and 406 are simultaneously lengthened and shortened as in the third embodiment, the inclusion of a mechanism to remove cord slack is advantageous. In particular, springs 1125 and 1126 exert forces on pins 1130 and 1131 in the direction away from knee joint 335. As a result, slack in cord loop 405 or cord loop 406 is taken up by movement of pin 1130 or pin 1131 away from knee joint 335. In alternative embodiments, other types of springs, or other mechanisms, can be used to remove cord slack. Also, motor 1100 and input shaft 1105 can be arranged differently. For example, motor 1100 and input shaft 1105 can be located below spindles 1120 and 1121, input shaft 1105 can be located between spindles 1120 and 1121, or there can be roller chain or some other mechanism linking the rotation of input shaft 1105 and spindles 1120 and 1121 in any of a number of ways known in the art.

The drive mechanism of the third embodiment is designed to be used with a brake mechanism such as those shown in the first and second embodiments of the present invention. In FIGS. 11A and 11B, a brake mechanism in accordance with the first embodiment is shown. Therefore, as discussed above, forward cord loop 405 passes through forward spindle 1120 and forward strand separator 410. Also, forward cord loop 405 is in contact with forward brake pulley 355, which rotates about forward pulley pin 415. Forward cord loop 405 is coupled to knee cam 360 of lower leg support 320 at a forward cord loop attachment point 420. Similarly, rearward cord loop 406 passes through rearward spindle 1121 and rearward strand separator 411. Also, rearward cord loop 406 is in contact with rearward brake pulley 356, which rotates about rearward pulley pin 415. Rearward cord loop 406 is coupled to knee cam 360 at rearward cord attachment point 521. Motor 1110 is connected to upper leg support 315 (as shown in FIGS. 3A and 3B) such that fixed distance is maintained between motors 1110 and knee joint 335. Gear 425 is coupled to knee cam 360, with gear 425 and knee cam 360 rotating together about knee joint 335. Forward brake assembly 430 includes forward brake pulley 355, forward pawl 435, forward pivot pin 440 and forward spring 445. Forward brake pulley 355 is rotatably coupled to forward pawl 435 by forward pulley pin 415. Rearward brake assembly 431 includes rearward brake pulley 356, rearward pawl 436, rearward pivot pin 441 and rearward spring 446. Rearward brake pulley 356 is rotatably coupled to rearward pawl 436 by rearward pulley pin 416. Forward brake assembly 430 and rearward brake assembly 431 are rotatably coupled to upper leg support 315 (shown in FIGS. 3A and 3B) at forward pivot pin 440 and rearward pivot pin 441. Forward spring 445 and rearward spring 446 are held under compression against upper leg support 315 by forward pawl 435 and rearward pawl 436. The force required to compress springs 445 and 446 is exerted by tensioned cord loops 405 and 406 against brake pulleys 355 and 356.

If breakage of rearward cord loop 406 occurs, rearward brake pulley 356 is no longer restrained by rearward cord loop 406, and rearward spring 446 causes rearward pawl 436 to rotate about rearward pivot pin 441 until rearward pawl 436 contacts gear 425. At this point, the teeth of rearward pawl 436 mate with the teeth of gear 425. Since rearward pawl 436 is coupled to upper leg support 315 and gear 425 is coupled to lower leg support 320, the mating of these teeth prevents lower leg support 320 and upper leg support 315 from rotating relative to one another at knee joint 335. In the context of FIGS. 3A and 3B, the locking of knee joint 335 fixes the relative positions of lower leg 345 and upper leg 346 of user 305.

Figure 12:
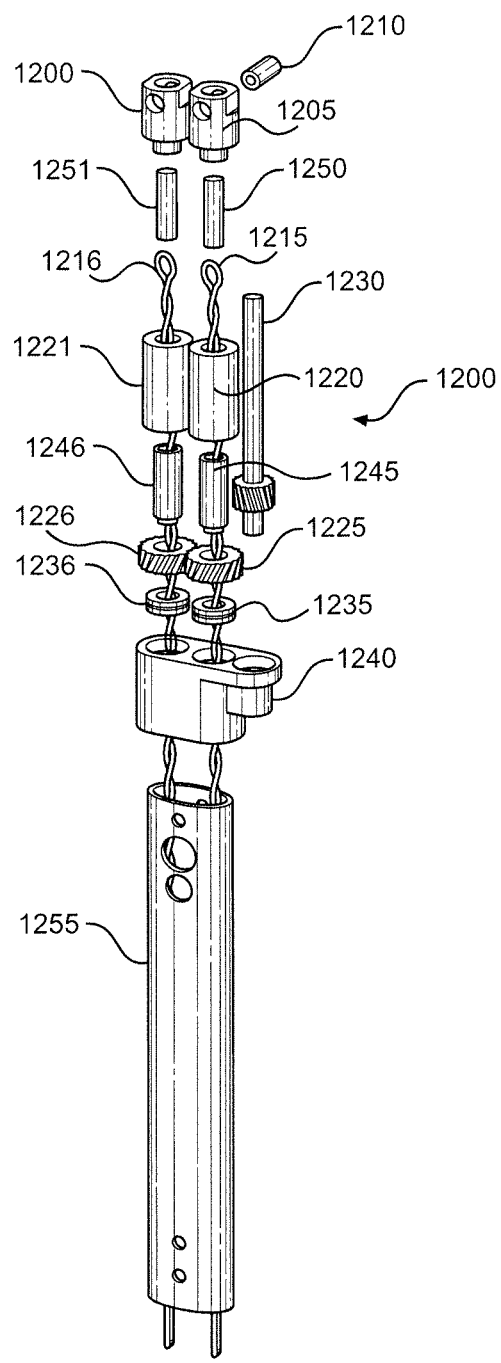
FIG. 12 is a detailed, exploded view of an actuator device constructed in accordance with the third embodiment of the present invention.

The actuator illustrated in FIGS. 11A and 11B is a somewhat simplified representation intended to facilitate an understanding of the present invention. A more detailed representation is provided in FIG. 12, which shows a device constructed in accordance with the third embodiment. Specifically, a device 1200 includes spindles 1205 and 1206, a spring termination pin 1210, cord loops 1215 and 1216, elastomer springs 1220 and 1221, helical gears 1225 and 1226, an input shaft 1230, thrust bearings 1235 and 1236, a drive mount bearing 1240, outer guide sleeves 1245 and 1246, inner guide sleeves 1250 and 1251 and extruded tubing 1255. The lower portions of device 1200 (i.e., the joint and brake mechanism) are not shown in FIG. 12 but are fundamentally similar to what is shown in FIG. 5. In device 1200, helical gears 1225 and 1226 are geared at a 1:1 ratio so that clockwise twist in one of spindles 1205 and 1206 is equally compensated for by counterclockwise twist in the other of spindles 1205 and 1206. In some embodiments, the spring tension is adjustable, either by changing out the springs or using other methods known in the art, to provide variable knee resistance.

As an example of the third embodiment, consider two exoskeleton devices. The first is equipped with the actuator of the first embodiment, and the second is equipped with the actuator of the third embodiment. The second exoskeleton requires only one electric motor per actuator, which allows for either reduced exoskeleton weight or increased motor size and torque at the same exoskeleton weight. Reducing the weight of an exoskeleton can increase the range and possible speed of the exoskeleton, among other advantages.

Increasing motor torque can increase exoskeleton speed as well as the lifting or load-bearing capacity of the exoskeleton.

Based on the above, it should be readily apparent that the present invention provides an exoskeleton in which an actuator makes use of a motor to twist a loop of cord in order to cause movement of an exoskeleton joint at a distance from the motor, with the joint being subject to bidirectional movements, and with movement of the joint being impeded in the event of cord loop breakage, thereby preventing injury to a wearer of the exoskeleton or further damage to the exoskeleton. The present invention also provides an exoskeleton in which a joint is subject to bidirectional movements through the action of a single motor. In addition, the present invention provides a device that controls the position and separation of the strands of the cord loop twisted by the actuator, with this device acting in such a way that the strands of the cord loop are subject to reduced wear with each twist cycle, thereby prolonging the functional lifespan of the cord loop. Although described with reference to preferred embodiments, it should be readily understood that various changes or modifications could be made to the invention without departing from the spirit thereof. In general, the invention is only intended to be limited by the scope of the following claims.

The invention claimed is:

1. An exoskeleton comprising:
a first support structure configured to be coupled to a wearer of the exoskeleton;
a second support structure configured to be coupled to the wearer of the exoskeleton;
a joint connecting the first and second support structures, the joint being configured to enable relative movement between the first and second support structures;
a first cord loop connecting the first and second support structures;
a second cord loop connecting the first and second support structures;
at least one motor configured to twist and thereby shorten the first and second cord loops, wherein shortening of the first cord loop causes relative pivotal movement of the first and second support structures about the joint in a first direction, and shortening of the second cord loop causes relative pivotal movement of the first and second support structures about the joint in a second, opposite direction; and
a brake configured to prevent relative movement of the first and second support structures about the joint in at least one of the first and second directions when one of the first and second cord loops breaks.

2. The exoskeleton of claim 1, wherein:
the brake includes a gear coupled to the second support structure;
the brake includes a first pawl coupled to the first support structure;
the brake is configured such that the first pawl contacts the gear when the first cord loop breaks; and
the brake is configured such that contact between the first pawl and the gear prevents relative movement of the first and second support structures about the joint in at least one of the first and second directions.

3. The exoskeleton of claim 2, wherein:
the brake includes a first pulley configured to contact the first cord loop;
the brake is configured such that contact between the first pulley and the first cord loop prevents contact between the first pawl and the gear;
the brake includes a first spring configured to apply a force to the first pawl; and
the brake is configured such that the first spring causes the first pawl to contact the gear when the first cord loop breaks.

4. The exoskeleton of claim 3, wherein:
the brake includes a second pawl;
the brake is configured such that the second pawl contacts the gear when the second cord loop breaks;
the brake is configured such that contact between the second pawl and the gear prevents relative movement of the first and second support structures about the joint in at least one of the first and second directions;
the brake includes a second pulley configured to contact the second cord loop;
the brake is configured such that contact between the second pulley and the second cord loop prevents contact between the second pawl and the gear;
the brake includes a second spring configured to apply a force to the second pawl; and
the brake is configured such that the second spring causes the second pawl to contact the gear when the second cord loop breaks.

5. The exoskeleton of claim 1, wherein the at least one motor includes a first motor configured to twist the first cord loop and a second motor configured to twist the second cord loop.

6. The exoskeleton of claim 1, wherein the at least one motor includes a single motor configured to simultaneously twist, in opposite rotational directions, both the first and second cord loops.

7. The exoskeleton of claim 6, further comprising an input shaft, a first spindle coupled to the first cord loop and a second spindle coupled to the second cord loop, wherein:
the single motor is configured to cause rotation of the input shaft;
the input shaft is configured to cause rotation of the first and second spindles;
the first spindle is configured to twist the first cord loop; and
the second spindle is configured to twist the second cord loop.

8. The exoskeleton of claim 7, further comprising:
a first spring configured to reduce slack in the first cord loop; and
a second spring configured to reduce slack in the second cord loop.

9. The exoskeleton of claim 1, further comprising a spindle coupled to one of the first and second cord loops, the spindle including a cord slot and a first cord guide, wherein the one of the first and second cord loops passes through the cord slot and contacts the first cord guide.

10. The exoskeleton of claim 9, wherein the first cord guide is wedge-shaped such that no gap exists between the first cord guide and a twisted helical cord structure of the one of the first and second cord loops when the one of the first and second cord loops is twisted by the at least one motor.

11. The exoskeleton of claim 9, further comprising a strand separator including a second cord guide, wherein:
the one of the first and second cord loops passes through the strand separator and contacts the second cord guide; and
the strand separator is configured such that a twisted helical cord structure of the one of the first and second cord loops only exists between the spindle and the strand separator when the one of the first and second cord loops is twisted by the at least one motor.

12. The exoskeleton of claim 11, wherein the second cord guide is wedge-shaped such that no gap exists between the second cord guide and the twisted helical cord structure when the one of the first and second cord loops is twisted by the at least one motor.

\* \* \* \* \*